US009068891B2

(12) United States Patent
Shioi et al.

(10) Patent No.: US 9,068,891 B2
(45) Date of Patent: Jun. 30, 2015

(54) METHOD AND APPARATUS FOR MEASURING CONCENTRATION OF BIOGENIC SUBSTANCE

(71) Applicants: Panasonic Corporation, Osaka (JP); IMEC vzw, Leuven (BE); Katholieke Universiteit Leuven, K.U. Leuven R&D, Leuven (BE)

(72) Inventors: Masahiko Shioi, Kyoto (JP); Kristof Lodewijks, Lommel (BE); Pol Van Dorpe, Spalbeek (BE); Hilde Jans, Heverlee (BE)

(73) Assignees: PANASONIC CORPORATION, Osaka (JP); IMEC vzw, Leuven (BE); Katholieke Universiteit Leuven, K.U.Leuven R&D, Leuven (BE)

( * ) Notice: Subject to any disclaimer, the term of this patent is extended or adjusted under 35 U.S.C. 154(b) by 128 days.

(21) Appl. No.: 13/734,600

(22) Filed: Jan. 4, 2013

(65) Prior Publication Data
US 2013/0176562 A1 Jul. 11, 2013

(30) Foreign Application Priority Data
Jan. 6, 2012 (JP) ................................. 2012-001479

(51) Int. Cl.
*G01J 3/44* (2006.01)
*G01N 21/65* (2006.01)

(52) U.S. Cl.
CPC ............. *G01J 3/4412* (2013.01); *G01N 21/658* (2013.01)

(58) Field of Classification Search
CPC ......... G01J 3/44; G01J 3/4412; G01N 21/658
USPC ........................................................ 356/301
See application file for complete search history.

(56) References Cited

U.S. PATENT DOCUMENTS

| 2009/0002701 A1 | 1/2009 | Fattal et al. |
| 2009/0118605 A1* | 5/2009 | Van Duyne et al. .......... 600/365 |

(Continued)

FOREIGN PATENT DOCUMENTS

| JP | 9-79982 | 3/1997 |
| JP | 2004-205435 | 7/2004 |

(Continued)

OTHER PUBLICATIONS

W. Rechberger et al., "Optical properties of two interacting gold nanoparticles", Optics Communications 220 (2003), pp. 137-141.
Alexandre Bouhelier et al., "Electromagnetic Interactions in Plasmonic Nanoparticle Arrays", J. Phys. Chem. B 2005, 109, pp. 3195-3198.
Yizhuo Chu et al., "Double-Resonance Plasmon Substrates for Surface-Enhanced Raman Scattering with Enhancement at Excitation and Stokes Frequencies", ACS Nano, vol. 4, No. 5, 2010, pp. 2804-2810.

(Continued)

*Primary Examiner* — Tarifur Chowdhury
*Assistant Examiner* — Sunghee Y Gray
(74) *Attorney, Agent, or Firm* — Wenderoth, Lind & Ponack L.L.P.

(57) ABSTRACT

A method for measuring a concentration of a biogenic substance in a living body includes steps of: preparing an apparatus including a light source, a substrate which has periodic metal structures and generates surface enhanced Raman scattering light by being irradiated with light from the light source, and spectroscopic means which disperses and detects the light, wherein the periodic metal structure is arranged with first and second distances in first and second direction respectively, the first distance is set to generate surface plasmon by matching a phase of the light from the light source, and the second distance is smaller than the first distance and is set between 300 nm and 350 nm; irradiating the substrate with the light from the light source to generate the surface enhanced Raman scattering; detecting the scattering with the spectroscopic means; and calculating the concentration of the biogenic substance based on the scattering.

5 Claims, 7 Drawing Sheets

(56) References Cited

U.S. PATENT DOCUMENTS

2011/0114859 A1* 5/2011 Amako et al. ............... 250/576
2011/0164252 A1 7/2011 Handa et al.

FOREIGN PATENT DOCUMENTS

| JP | 2007-101308 | 4/2007 |
| JP | 2008-25989 | 2/2008 |
| JP | 2009-85724 | 4/2009 |
| JP | 2010-531995 | 9/2010 |
| WO | 2009/002524 | 12/2008 |
| WO | 2009/041709 | 4/2009 |

OTHER PUBLICATIONS

Melissa F. Mrozek et al., "Detection and Identification of Aqueous Saccharides by Using Surface-Enhanced Raman Spectroscopy", Analytical Chemistry, vol. 74, No. 16, Aug. 15, 2002, pp. 4069-4075.

Chanda Ranjit Yonzon et al., "A Glucose Biosensor Based on Surface-Enhanced Raman Scattering: Improved Partition Layer, Temporal Stability, Reversibility, and Resistance to Serum Protein Interference", Analytical Chemistry, vol. 76, No. 1, Jan. 1, 2004, pp. 78-85.

* cited by examiner

METHOD AND APPARATUS FOR MEASURING CONCENTRATION OF BIOGENIC SUBSTANCE

BACKGROUND OF THE INVENTION

1. Field of the Invention

The present invention relates to a method for measuring a concentration of a biogenic substance and a measuring apparatus used for the method, particularly a method for measuring a concentration of a biogenic substance such as glucose contained in a living body, and a measuring apparatus used for the method.

2. Description of the Related Art

A concentration of a biogenic substance such as glucose contained in a living body is measured based on reflected light, scattered light or transmitted light of light radiated on the living body. More specifically, Raman scattering of the biogenic substance is observed, and the concentration of the biogenic substance is calculated based on the intensity of the Raman scattering.

Conventionally, Raman spectroscopy has been used in various applications and, for example, there is a disclosed technique for measuring a concentration of a biogenic substance by using Raman spectroscopy (for example, see JP 9-079982 A). The use of Raman spectroscopy can eliminate the need for consumables such as reagents, test strips, and enzymes in order to determine the concentration of a characteristic substance in biogenic substances; further eliminate the problem of preservation stability of the consumables before use, the problem of disposal of the consumables after use, and the problems of cumbersome operations contributing to errors and interferences from other substances; and moreover quantitatively measure multiple substances at once.

As a method of surface enhanced Raman spectroscopy, there is a disclosed technique which allows a surface enhanced Raman scattering substrate made of a group of noble metal colloids to coexist with a Raman active substance having stoichiometric relation with a substance to be analyzed, and measuring surface enhanced Raman scattering due to its enhanced electric field (for example, see JP 2004-205435 A). According to this technique, surface enhanced Raman scattering can be excited efficiently by light with a wavelength in the near-infrared region. By exciting surface enhanced Raman scattering with light in the near-infrared region and performing analysis by Raman spectroscopy in the near-infrared region, it is possible to eliminate effects of light absorption and fluorescence of foreign substances in a matrix in which the substance to be analyzed is contained, and improve specificity and selectivity in detection of the substance to be analyzed.

JP 2010-531995 A sets the size and shape of a nanofeature and the distance between nanofeatures such that an excitation frequency $\omega$, a planar mode $\omega spp$, and a localized surface plasmon mode $\omega LSP$ are equal, thereby exciting both the planar mode $\omega spp$ and the localized surface Plasmon mode $\omega LSP$. Thus, the planar mode and the localized surface plasmon mode constructively interfere with each other to generate an electromagnetic wave having an electric field that is greater than either the enhanced electric field due to the localized surface plasmon mode or the planar mode, individually.

There is a disclosed method of increasing the enhanced factor of surface enhanced Raman scattering by arranging metal nanoparticles in the tetragonal lattice in Yizhuo Chu, Mohamad G. Banaee, and Kenneth B. Crozier, "Double-Resonance Plasmon Substrates for Surface-Enhanced Raman Scattering with Enhancement at Excitation and Stokes Frequencies", ACS Nano, Vol. 4, No. 5, 2804-2810, 2010. According to the method, the distance between metal nanoparticles is appropriately set, whereby the electric field of laser light that excites surface enhanced Raman scattering is increased by plasmon resonance due to a grating effect; and the metal nanoparticles are provided such that the wavelength region of localized surface plasmon resonance by the metal nanoparticles themselves is matched to the position of the wavelength region of the generated Raman scattering, whereby the surface enhanced Raman scattering is very strongly enhanced.

SUMMARY OF THE INVENTION

An object of the present invention is to provide a method for measuring a concentration of a biogenic substance with improved measurement accuracy.

The present invention provides a method for measuring a concentration of a biogenic substance, including the following steps (a) to (d): (a) preparing an apparatus for biogenic substance concentration measurement, the apparatus including a light source, a substrate which has periodic metal structures and generates surface enhanced Raman scattering light by being irradiated with light emitted from the light source, and spectroscopic means which disperses and detects the surface enhanced Raman scattering light, wherein the periodic metal structure is arranged with a first distance in a first direction and with a second distance in a second direction, the first distance is set to generate surface plasmon by matching a phase of the light emitted by the light source, and the second distance is smaller than the first distance and the second distance is set between 300 nm and 350 nm; (b) irradiating the substrate with the light emitted from the light source so as to generate the surface enhanced Raman scattering; (c) detecting the generated surface enhanced Raman scattering with the spectroscopic means; and (d) calculating the concentration of the biogenic substance on the basis of the surface enhanced Raman scattering detected in the step (c).

Further, the present invention provides a method for measuring a concentration of a biogenic substance, including the following steps (a) to (j): (a) preparing an apparatus for biogenic substance concentration measurement, the apparatus including a light source, a polarization controller which controls a polarization of the light from the light source, a substrate which has periodic metal structures and generates surface enhanced Raman scattering light by being irradiated with light emitted from the light source, and spectroscopic means which disperses and detects the surface enhanced Raman scattering light, wherein the periodic metal structure is arranged with a first distance in a first direction and with a second distance in a second direction, the first distance is set to generate surface plasmon by matching a phase of the light emitted by the light source, and the second distance is smaller than the first distance and the second distance is set between 300 nm and 350 nm; (b) irradiating the substrate with the light emitted from the light source so as to generate the surface enhanced Raman scattering, wherein the polarization of the light is controlled along with the first direction by the polarization controller; (c) detecting the generated surface enhanced Raman scattering with the spectroscopic means; (d) recording an intensity of the surface enhanced Raman scattering detected in step (c); (e) irradiating the substrate with the light emitted from the light source so as to generate the surface enhanced Raman scattering, wherein the polarization of the light is changed by the polarization controller; (f) detecting the generated surface enhanced Raman scattering at the step (e) with the spectroscopic means; (g) recording an intensity of the surface enhanced Raman scattering detected in step (f); (h) determining a larger intensity of surface enhanced Raman scattering and recording the larger intensity by comparing the recorded intensity of the surface enhanced Raman scattering at the step (g) with the recorded intensity of the surface enhanced Raman scattering at step (d); (i) calculating the maximum intensity of surface enhanced Raman scattering by repeating the steps of (e) to (h); (j) calculating the concentration of the biogenic substance on the basis of the maximum intensity of surface enhanced Raman scattering calculated in the step (i).

Further, the present invention provides an apparatus for biogenic substance concentration measurement including: a light source, a substrate which has periodic metal structures and generates surface enhanced Raman scattering light by being irradiated with light emitted from the light source, and spectroscopic means which disperses and detects the surface enhanced Raman scattering light, wherein the periodic metal structure is arranged with a first distance in a first direction and with a second distance in a second direction, the first distance is set to generate surface plasmon by matching a phase of the light emitted by the light source, and the second distance is smaller than the first distance and the second distance is set between 300 nm and 350 nm.

Further, the present invention provides an apparatus for biogenic substance concentration measurement including: a light source, a polarization controller which controls a polarization of the light from the light source, a substrate which has periodic metal structures and generates surface enhanced Raman scattering light by being irradiated with light emitted from the light source, and spectroscopic means which disperses and detects the surface enhanced Raman scattering light, wherein the periodic metal structure is arranged with a first distance in a first direction and with a second distance in a second direction, the first distance is set to generate surface plasmon by matching a phase of the light emitted by the light source, and the second distance is smaller than the first distance and the second distance is set between 300 nm and 350 nm.

The present invention provides a method for measuring a concentration of a biogenic substance with improved measurement accuracy.

DETAILED DESCRIPTION OF THE PREFERRED EMBODIMENTS

First Embodiment

Hereinafter, a method for measuring a concentration of a biogenic substance according to a first embodiment will be explained with reference to drawings.

Step (a)

Figure 1:
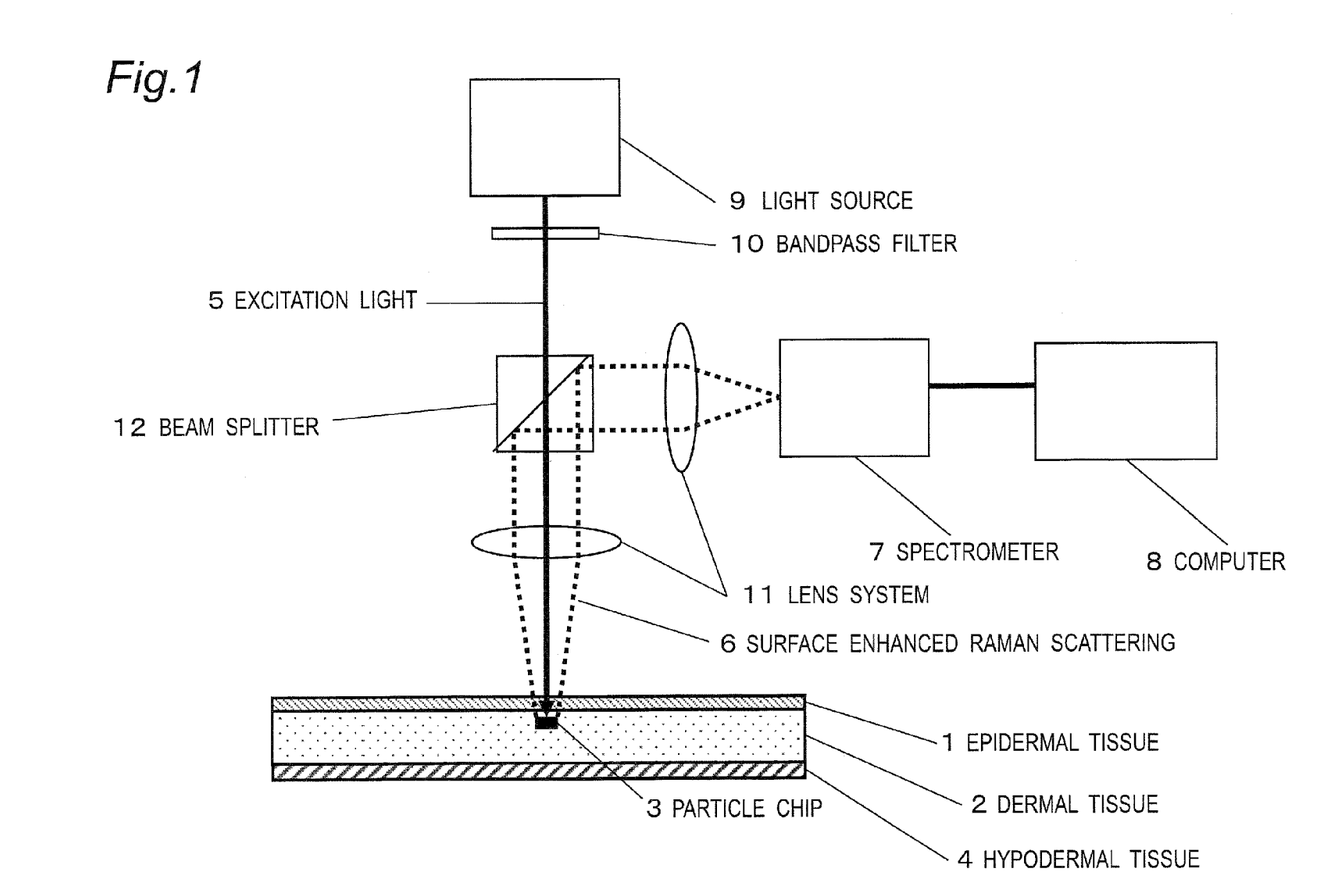
FIG. 1 is a schematic diagram showing the configuration of a measurement apparatus according to a first embodiment of the present invention.

In step (a), a measurement apparatus is prepared. As shown in FIG. 1, the measurement apparatus includes a light source 9 and a spectrometer 7. The measurement apparatus includes a bandpass filter 10, a lens system 11, a beam splitter 12, and a computer 8 as required. A particle chip 3 is implanted into a dermal tissue 2 beforehand as shown in FIG. 1.

Figure 2:
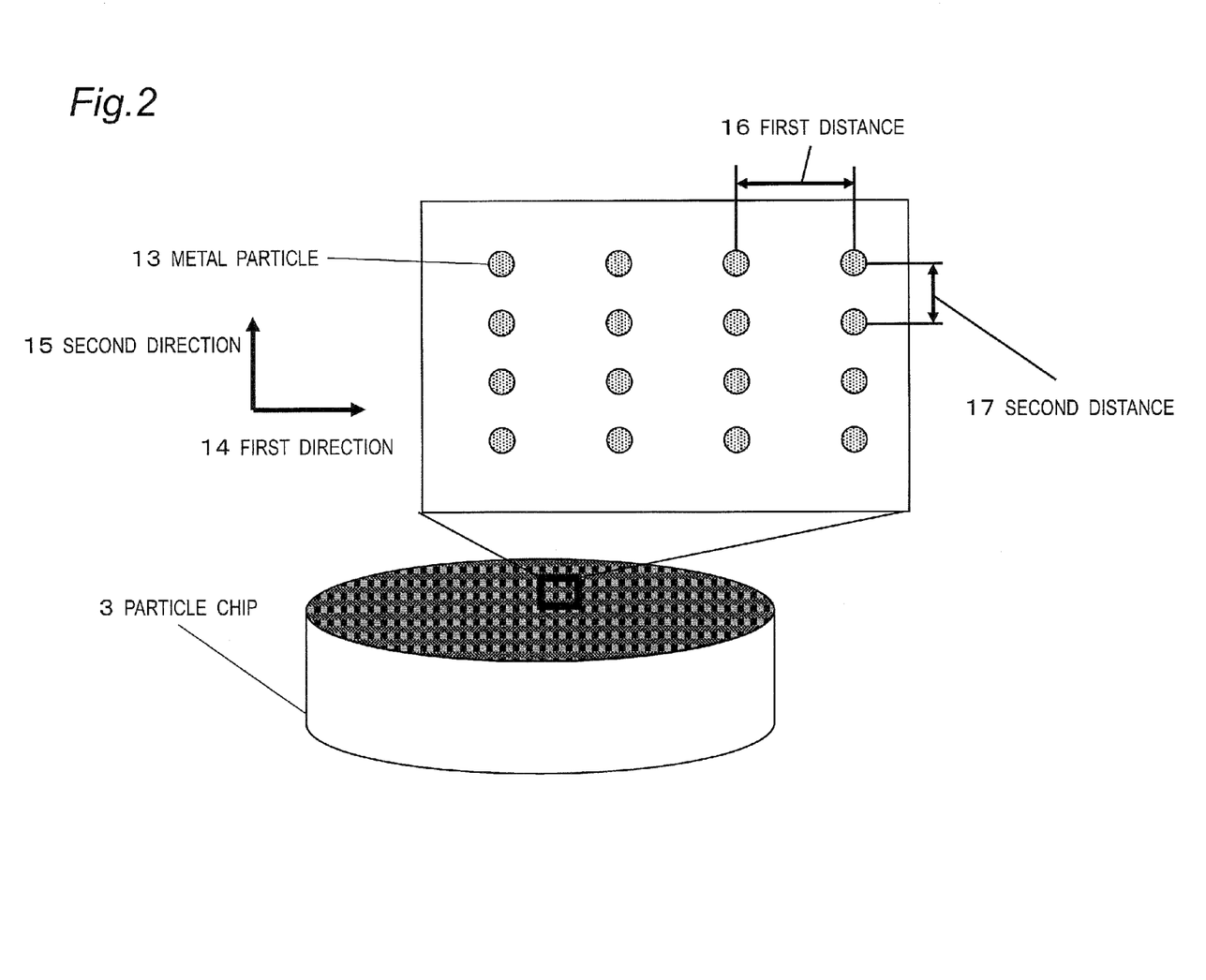
FIG. 2 shows a particle chip 3.

FIG. 2 shows the particle chip 3 and its partial enlarged view. Metal particles 13 are provided on the surface of the particle chip 3. The metal particles 13 are arranged with the first distance 16 in the first direction 14 and with the second distance 17 in the second direction 15. The first distance 16 is set to generate surface plasmon polariton due to grating effects by matching the phase of the light from the light source 9. Specifically, the first distance 16 is determined by the following equation (I).

$$\vec{k}_{SPP} = \frac{2\pi}{a} = \frac{2\pi}{\lambda_0} N \quad (I)$$

a: First distance 16
$\lambda_0$: Wavelength of light radiated from light source
N: Effective refractive index Here, the effective refractive index N is determined by the refractive index of a material of a substrate of the particle chip 3 and the refractive index on the periphery of the particle chip 3.

For example, when the wavelength of light radiated from the light source 9 is 785 nm and the effective refractive index is 1.35, the first distance 16 is about 580 nm. Accordingly, surface plasmon polariton which is necessary for generating surface enhanced Raman scattering with respect to the excitation light 785 nm radiated from the light source 9 is generated by matching the wave number vector of surface plasmon polariton described in the equation (I) with the wave number vector of diffracted light generated by diffraction of the excitation light radiated from the light source 9, the diffraction brought by the metal particles 13 arranged at a distance of about 580 nm from one another. When the surface Plasmon polariton is generated, the polarization component of light from the light source 9 should include a component corresponding to the first direction 14.

It is known that the intensity of surface enhanced Raman scattering is proportional to the square of the electric field intensity of the excitation light and the square of the electric field intensity in the Raman radiation region and also proportional to the number of molecules that generate surface enhanced Raman scattering.

Next, the second distance will be considered. The second distance 17 is narrower than the first distance 16, so that the number of metal particles 13 illuminated by the excitation light radiated from the light source 9 increases. Thus, the number of molecules that generate surface enhanced Raman scattering increases. In this manner, the second distance 17 is set to be narrower than the first distance 16 to improve the density of the layout of the metal particles 13, leading to increase in the number of molecules that generate surface enhanced Raman scattering and increase in the intensity of the surface enhanced Raman scattering 6.

One example of the metal particle 13 is a gold nanodisk with 130 nm in diameter and 30 nm in height. In place of the gold nanodisk, a dielectric particle which has a surface coated with a metal such as gold or silver may be used. Examples of the dielectric particle include silica.

The metal particle 13 has a surface plasmon resonance wavelength, of 785 nm and a localized surface plasmon resonance wavelength of 860 nm. The terms "surface Plasmon resonance wavelength" and "localized surface Plasmon resonance wavelength" used herein refer to the wavelength of a dip in reflectance due to surface Plasmon resonance or localized surface Plasmon resonance observed in measuring the reflectance of a substrate.

Figure 3:
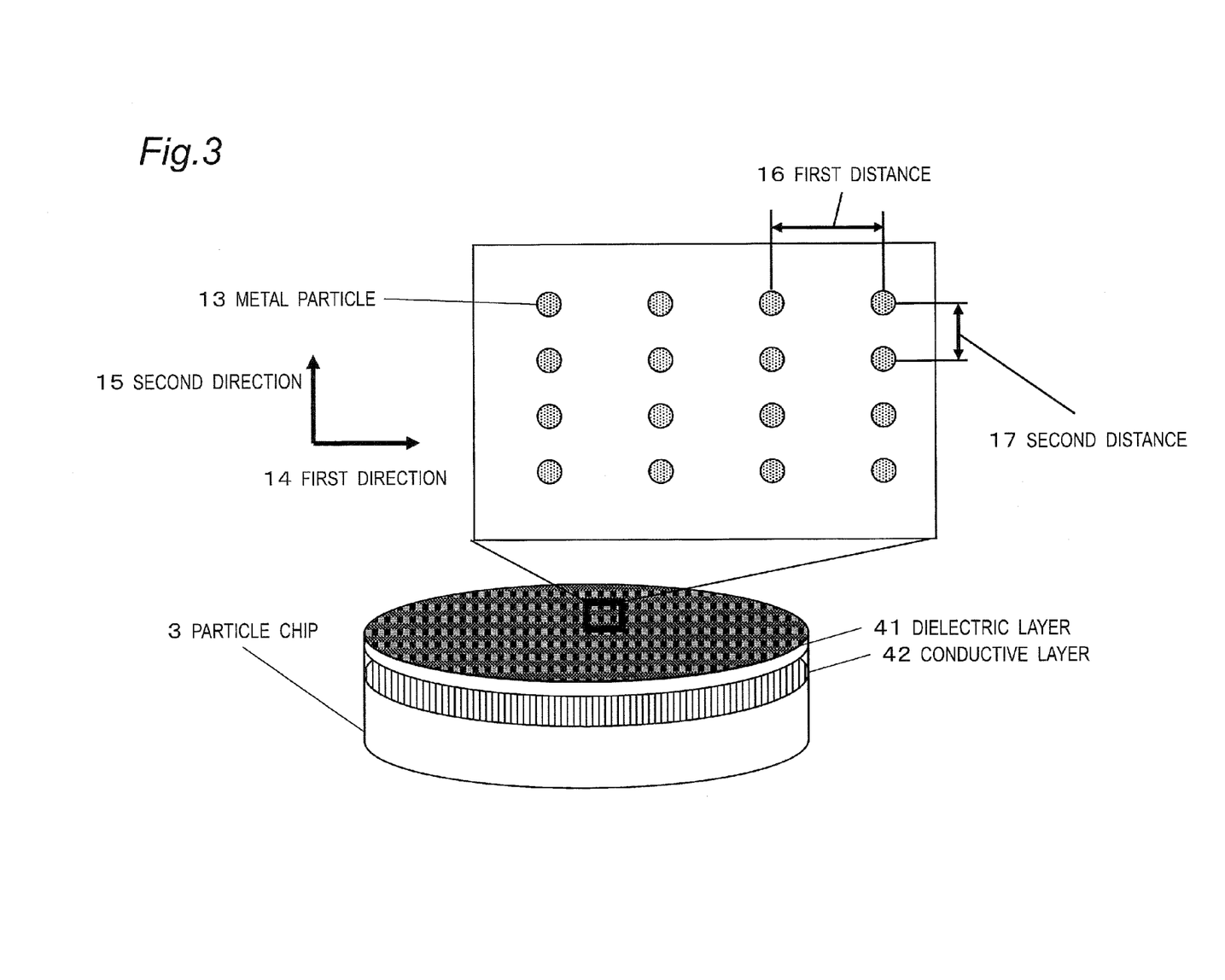
FIG. 3 shows another configuration example of the particle chip 3.

The substrate has approximately 100 μm in diameter and approximately 100 μm in thickness. Examples of the material of the substrate include a resin such as an acryl resin, glass, and silicon. As shown in FIG. 3, it is possible to form a conductive layer 42 on the substrate, form a dielectric layer 41 thereon, and provide the metal particles 13 thereon. In this manner, electric quadrupole resonance is generated between the metal particles 13 and the conductive layer 42, so that the electric field due to the generated localized surface plasmon polariton is more likely to be confined on the periphery of the metal particles, resulting in the electric field enhancement effect being expected to rise to a further extent, thus being preferred.

For example, a material such as gold, silver, and platinum can be used as the conductive layer 42, and a material such as silicon oxide, titanium oxide, and aluminum oxide can be used as the dielectric layer 41. For example, gold can be used as one example of the conductive layer 42, and silicon oxide can be used as one example of the dielectric layer 41. One example of the thickness of the gold thin film is 100 nm and one example of that of the silicon oxide thin film is 30 nm. In order to further improve adhesiveness between the conductive layer 42 and the substrate, a metal thin film such as titanium, titanium-tungsten, and chromium may be provided between the conductive layer 42 and the substrate.

Figure 4:
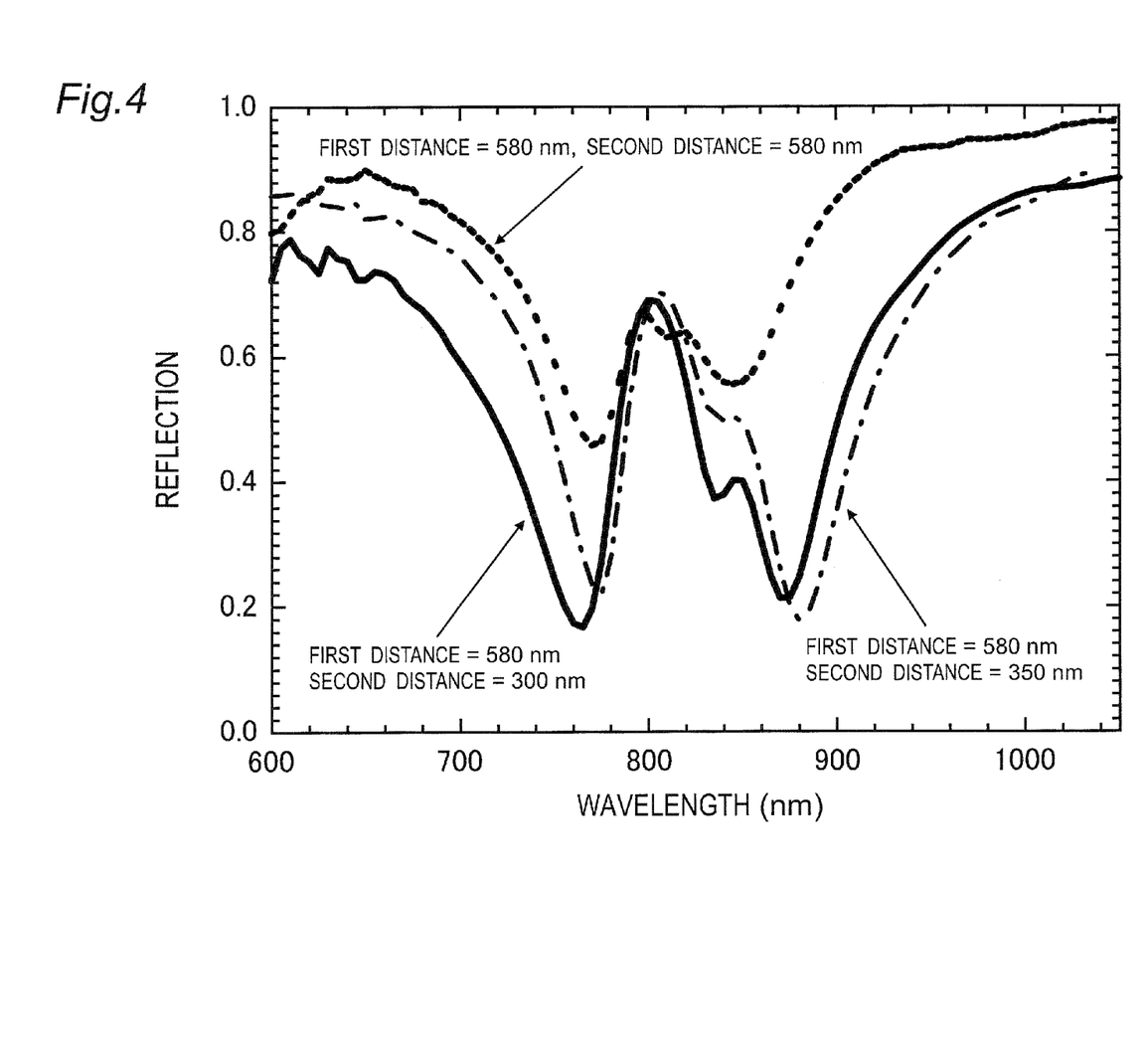
FIG. 4 is one example of measurement results of the reflectance of the particle chip 3.

FIG. 4 shows measurement results of the reflectance of the particle chip 3 in water. In FIG. 4, the dashed line shows the reflectance of a particle chip demonstrating a conventional example in which gold nanodisks are arranged in the tetragonal lattice (first distance=580 nm, second distance=580 nm), and the solid line and the chain line show the reflectance of the particle chip 3 used in the first embodiment (solid line: first distance=580 nm, second distance=300 nm; and chain line: first distance=580 nm, second distance=350 nm). The particle chip is prepared by forming a gold thin film of 100 nm and a silicon oxide thin film of 30 nm on a substrate and placing gold nanodisks on the silicon oxide thin film. The dip in reflectance in the vicinity of 785 nm shows the position of the surface plasmon resonance wavelength, and the dip in reflectance in the vicinity of 860 nm shows the position of the localized surface plasmon resonance wavelength. The small reflectances mean that the electric field enhancement of the surface Plasmon resonance and the localized surface Plasmon resonance are large. In FIG. 4, it is shown that the reflectance of the particle chip 3 of the first embodiment is smaller than that of the conventional example. Accordingly, it is shown that the particle chip 3 of the first embodiment has a larger electric field enhancement effect than that of the conventional example.

Figure 5:
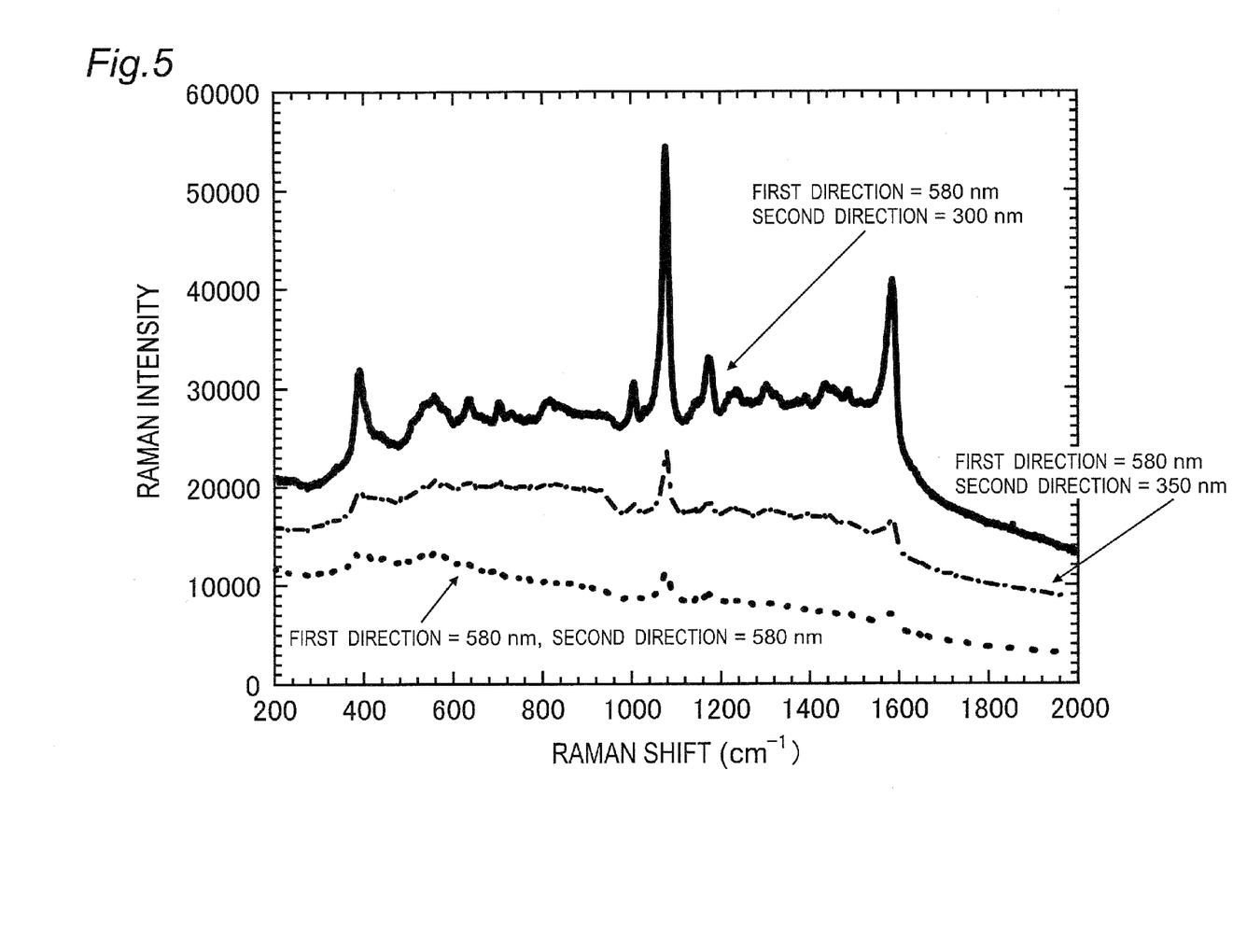
FIG. 5 is one example of measurement results of surface enhanced Raman scattering.

FIG. 5 shows measurement results of 4-aminothiophenol with the particle chip 3 in water as one example of measurement results of surface enhanced Raman scattering. In FIG. 5, the dashed line shows a measurement result of surface enhanced Raman scattering of 4-aminothiophenol with a particle chip demonstrating a conventional example in which gold nanodisks are arranged in the tetragonal lattice (first distance=580 nm, second distance=580 nm), and the solid line and the chain line show measurement results of surface enhanced Raman scattering of 4-aminothiophenol with the particle chip 3 used in the first embodiment (solid line: first distance=580 nm, second distance=300 nm; and chain line: first distance=580 nm, second distance=350 nm). As explained in FIG. 4, it is shown that the particle chip 3 of the first embodiment has a larger electric field enhancement effect than that of the conventional example, and therefore also has a higher enhanced degree of surface enhanced Raman scattering. In FIG. 4, when comparison is made between the case where the second distance is 300 nm and the case where it is 350 nm, the reflectance at the resonance position due to surface plasmon polariton in the vicinity of 765 nm, which is the wavelength of the excitation light, is smaller in the case where the second distance is 350 nm. Accordingly, the enhancement factor of surface enhanced Raman scattering resulting from the electric field enhancement of the excitation light is larger in the case where the second distance is 350 nm. However, the reflectance at the resonance position due to localized surface plasmon polariton in the Raman radiation region 850 to 870 nm is smaller in the case where the second distance is 300 nm. Accordingly, the enhancement effect of surface enhanced Raman scattering resulting from the electric field enhancement due to localized surface plasmon resonance is larger in the case where the second distance is 300 nm. Furthermore, the number of metal particles 13 illuminated by the excitation light is larger in the case where the second distance is 300 nm, so that the effect is larger in the case where the second distance is 300 nm. From the above, the second distance may be 300 to 350 nm, and preferably 300 nm.

Step (b) or Step (b')

In step (b), as shown in FIG. 1, the excitation light 5 radiated from the light source 9 is transmitted through the bandpass filter 10 and then through the surface of a skin. The particle chip 3 implanted into the skin is irradiated by the transmitted light to generate surface enhanced Raman scattering 6 there.

The polarization of the excitation light 5 radiated from the light source 9 needs to correspond to the first direction 14, so that a light source that irradiates non-polarization light is selected as the light source 9. Alternatively, when a light source 9 that radiates light having a certain polarization is used, the polarization of the excitation light 5 is set to correspond to the first direction beforehand (Step (b')).

As a polarization controller, when the light source 9 that radiates non-polarization light is used, a known polarizer can be used. Alternatively, when the light source 9 that radiates light having a certain polarization is used, the polarization can be controlled by using, for example, a rotation device such as a motor to rotate the light source.

Step (c)

In step (c), as shown in FIG. 1, the generated surface enhanced Raman scattering 6 is focused by the lens system 11, reflected by the beam splitter 12, focused by the lens system 11, and then detected by the spectrometer 7.

For the spectrometer 7, any known technique can be used without any limitation. For example, a Czerny-Turner spectrometer, an Echelle spectrometer, a flat field spectrometer, a filter spectrometer, and the like can be used.

As shown in FIG. 1, the skin includes an epidermal tissue 1, a dermal tissue 2, and a subcutaneous tissue 4. The epidermal tissue 1, dermal tissue 2, and subcutaneous tissue 4 are stacked in this order.

The epidermal tissue 1 is located at the surface of the living body. The epidermal tissue 1 has a thickness of approximately 0.2 to 0.5 mm. The dermal tissue 2 has a thickness of approximately 0.5 to 2 mm. The particle chip 3 is implanted into the dermal tissue 2 and maintained while being immersed in an interstitial fluid, which is a body fluid between tissue cells. The subcutaneous tissue 4 is constituted mainly of adipose tissue.

Because the dermal tissue 2 has a plurality of blood capillaries, the body fluid contains biogenic substances in the blood capillaries. In particular, since glucose has high osmosis, the glucose concentration in the body fluid is highly correlated with blood sugar level.

As shown in FIG. 1, the particle chip 3 is implanted into the dermal tissue 2 such that the plane which includes the metal particles 13 is parallel to the epidermal tissue 1. The distance from the epidermal tissue 1 to the particle chip 3 is approximately 1.5 mm.

When the particle chip 3 is irradiated with the excitation light 5, surface plasmon resonance is generated on the metal particles 13 to enhance the electromagnetic field intensity on the periphery of the metal particles 13. This causes Raman scattering of the biogenic substance located on the periphery (within 0.5 to 30 nm) of the metal particles 13 to be enhanced. Thus, surface enhanced Raman scattering 6 is generated. Since the enhancement effect of the surface enhanced Raman scattering 6 is proportional to the product of the electric field enhancement effect of the excitation light 5 and the electric field enhancement effect of the Raman scattering wavelength, it is preferred that the surface plasmon resonance wavelength corresponds to the wavelength of the excitation light 5 and that the localized surface plasmon resonance wavelength corresponds to the Raman scattering wavelength of, for example, glucose.

For measuring the surface enhanced Raman scattering of glucose, for example, a self-assembled monolayer film of 11-mercapto undecanol triethylene glycol ether may be provided on the metal particles 13 in order to temporarily maintain glucose on the periphery of the metal particles 13, as shown in Chanda Ranjit Yonzon, Cristy L. Haynes, Xiaoyu Zhang, Joseph T. Walsh, Jr., Richard P. Van Duyne, "A Glucose Biosensor Based on Surface-Enhanced Raman Scattering: Improved Partition Layer, Temporal Stability, Reversibility, and Resistance to Serum Protein Interference", Analytical Chemistry, Vol. 76, 78-85, 2004. In this manner, not only glucose is maintained on the periphery of the metal particles 13, but also a large number of proteins existing in the living body can be prevented from being adsorbed in the particle chip 3.

The intensity of the surface enhanced Raman scattering is $10^4$ to $10^9$ times greater than the intensity of normal Raman scattering. Accordingly, the surface enhanced Raman scattering generated on the periphery of the metal particles 13 has significantly greater intensity than the Raman scattering generated in the skin surface (including the corneum), in the epidermal tissue 1, or in the dermal tissue 2. This means that the Raman scattering derived from a biogenic substance contained in a body fluid on the periphery of the metal particles 13 is selectively enhanced. Thus, the influence of the stray light and the interruption substance is lowered.

The amount of the biogenic substance such as glucose contained in a living body is significantly lower than the amount of the interruption substance contained in the living body. Accordingly, normal Raman scattering of glucose has significantly smaller intensity than the Raman scattering of the interruption substance contained in the skin surface (the corneum in the epidermal tissue 1), in the epidermal tissue 1, or in the dermal tissue 2. For this reason, it is hard to extract the normal Raman scattering of glucose.

However, the particle chip 3 can selectively enhance the Raman scattering of glucose contained in a body fluid of the dermal tissue 2 on the periphery of the metal particles 13. This increases the intensity of the Raman scattering of glucose selectively, compared to the intensity of the Raman scattering of the interruption substance. Since the intensity of the surface enhanced Raman scattering of glucose is proportional to the concentration of glucose, the concentration of glucose can be calculated from the intensity of the surface enhanced Raman scattering of glucose.

Step (d)

One example of calculating the concentration of glucose is described below.

The surface enhanced Raman scattering spectrum of glucose is shown in FIG. 1 of Chanda Ranjit Yonzon, Cristy L. Haynes, Xiaoyu Zhang, Joseph T. Walsh, Jr., Richard P. Van Duyne, "A Glucose Biosensor Based on Surface-Enhanced Raman Scattering Improved Partition Layer, Temporal Stability, Reversibility, and Resistance to Serum Protein Interference", Analytical Chemistry, Vol. 76, 78-85, 2004. As described in FIG. 1 of the above document, the surface enhanced Raman scattering spectrum of glucose has a plurality of peaks specific to glucose in the Raman shift range of 1000 $cm^{-1}$ to 1500 $cm^{-1}$.

Among the plurality of peaks, the peak having a Raman shift of 1120 ($cm^{-1}$) does not overlap the peaks of the Raman scattering spectra of albumin and creatinine. Accordingly, the intensity of the surface enhanced Raman scattering with the Raman shift of 1120 ($cm^{-1}$) is proportional only to the concentration of glucose.

When the wavelength of the excitation light 5 is 785 nm, a filter 13 through which light having a wavelength of 860.7 nm is to be transmitted is used. The wavelength of 860.7 nm corresponds to the wave number that is smaller than the wave number corresponding to the wavelength of 785 nm by 1120 $cm^{-1}$.

The relationship between wavelength λ and wave number k satisfies the following equation (II):

$$k(cm^{-1}) = 10^7 / \lambda(nm) \quad (II)$$

The value obtained by converting a wavelength λ of 785 nm into the wave number k is 12739 ($cm^{-1}$). The wave number of the peak specific to glucose is smaller than 12739 ($cm^{-1}$) by 1120 ($cm^{-1}$). Accordingly, the wave number is calculated by the following equation: 12739 ($cm^{-1}$)−1120 ($cm^{-1}$)=11619 ($cm^{-1}$). The value obtained by converting a wave number of 11619 ($cm^{-1}$) into the wavelength is 860.7 nm.

The surface enhanced Raman scattering 6 is dispersed by the spectrometer 7. For example, for the spectrum of 1000 to 1500 $cm^{-1}$ specific to glucose dispersed by the spectrometer 7, a standard curve prepared beforehand is used to calculate the concentration of glucose. As a method of making the standard curve, for example, the Partial Least Squares algorithm may be used.

As described above, by using the measurement apparatus according to the first embodiment, the concentration of a biogenic substance such as glucose can be calculated.

Second Embodiment

Figure 6:
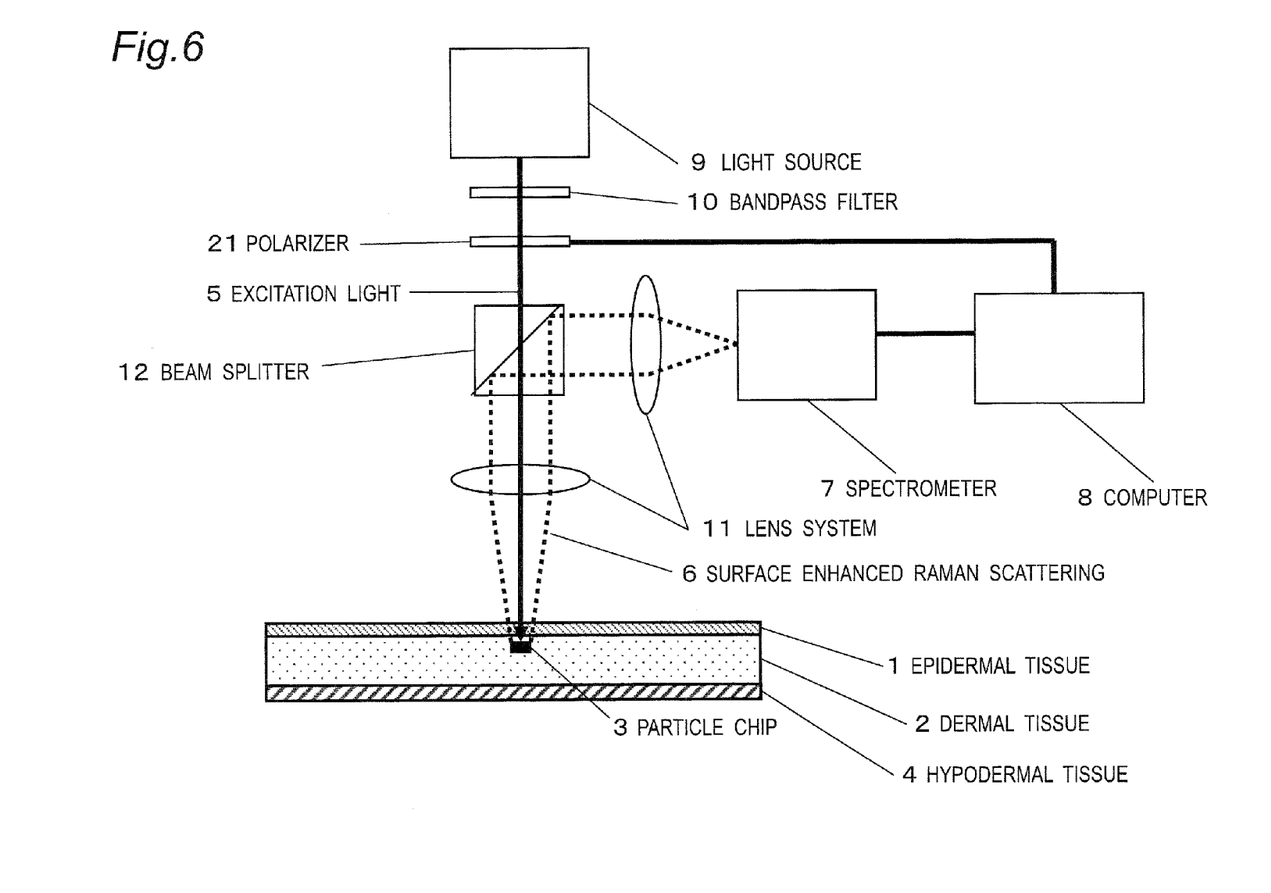
FIG. 6 is a schematic diagram showing the configuration of a measurement apparatus according to a second embodiment of the present invention.

Hereinafter, a method for measuring a concentration of a biogenic substance according to a second embodiment will be explained with reference to FIG. 6. In FIG. 6, the same components as those in FIG. 1 are denoted by the same numerals, and descriptions thereof are omitted.

FIG. 6 is a schematic diagram showing the configuration of a measurement apparatus according to the second embodiment.

Step (a) and Step (b)

In step (a), a measurement apparatus is prepared. As shown in FIG. 6, the measurement apparatus includes a light source 9, a polarizer 21, a computer 8, and a spectrometer 7. The measurement apparatus includes a bandpass filter 10, a lens system 11, and a beam splitter 12 as required. A particle chip 3 is implanted into a dermal tissue 2 beforehand as shown in FIG. 6. The particle chip 3 may be the same as in the first embodiment.

The polarizer 21 which includes a rotation device such as a stepping motor (not shown) and to which the computer 8 is connected constitutes a polarization controller of the present invention.

As the polarization controller, for example, when a light source 9 that radiates non-polarization light is used, a known polarizer can be used. Alternatively, when a light source 9 that radiates light having a certain polarization is used, the polarization can be controlled by using, for example, a rotation device such as a motor to rotate the light source (not shown).

The computer 8 drives the polarizer 21 and transfers it to an initial position. At this time, the initial position of the polarizer 21 is preferably controlled along with the first direction 14 because the measurement time can be shortened.

In step (b), as shown in FIG. 6, the excitation light 5 radiated from the light source 9 is transmitted through the bandpass filter 10 and the polarizer 21 and then through the surface of the skin. The particle chip 3 implanted into the skin is irradiated with the transmitted light to generate surface enhanced Raman scattering 6 there.

Step (c) to Step (g)

In step (c), the surface enhanced Raman scattering 6 generated in step (b) is detected by the spectrometer 7.

In step (d), the intensity of the surface enhanced Raman scattering detected in step (c) is stored in the computer 8.

In step (e), the motor is driven based on the instruction from the computer 8, thereby driving the polarizer 21. In this manner, the polarization state of the excitation light 5 radiated from the light source 9 is changed. In this state, the particle chip 3 is irradiated with the excitation light 5 again to generate surface enhanced Raman scattering 6.

In step (f), the surface enhanced Raman scattering 6 generated in step (e) is detected by the spectrometer 7.

In step (g), the intensity of the surface enhanced Raman scattering detected in step (f) is recorded in the computer 8.

Step (h)

In step (h), the intensity of the surface enhanced Raman scattering recorded in step (g) is compared with the intensity of the surface enhanced Raman scattering recorded in step (d), thereby determining a larger intensity of surface enhanced Raman scattering 6 and recording the result by associating the state of the polarizer 21 at the time with the intensity of the surface enhanced Raman scattering.

Step (i)

In step (i), the maximum intensity of surface enhanced Raman scattering is calculated by repeating the steps of (e) to (h).

Step (j)

In step (j), the concentration of glucose is calculated based on the maximum intensity of surface enhanced Raman scattering detected in step (i). At this time, the method of calculating the concentration of glucose can be the same method as in step (d) in the first embodiment.

In the second embodiment, there has been explained a method of using the light source 9 of non-polarization light and driving the polarizer 21 to change the polarization state of the excitation light 5; however, as a method of changing the polarization state, when the light source 9 that radiates light having a certain polarization is used as described above, there may be employed a method in which the polarization is controlled by using, for example, a rotation device such as a motor to rotate the light source.

In the second embodiment, the surface enhanced Raman scattering 6 is measured while changing the polarization state of the excitation light 5, and the maximum intensity is used for calculation of the concentration of glucose, thereby achieving higher accuracy of measurement.

Third Embodiment

Figure 7:
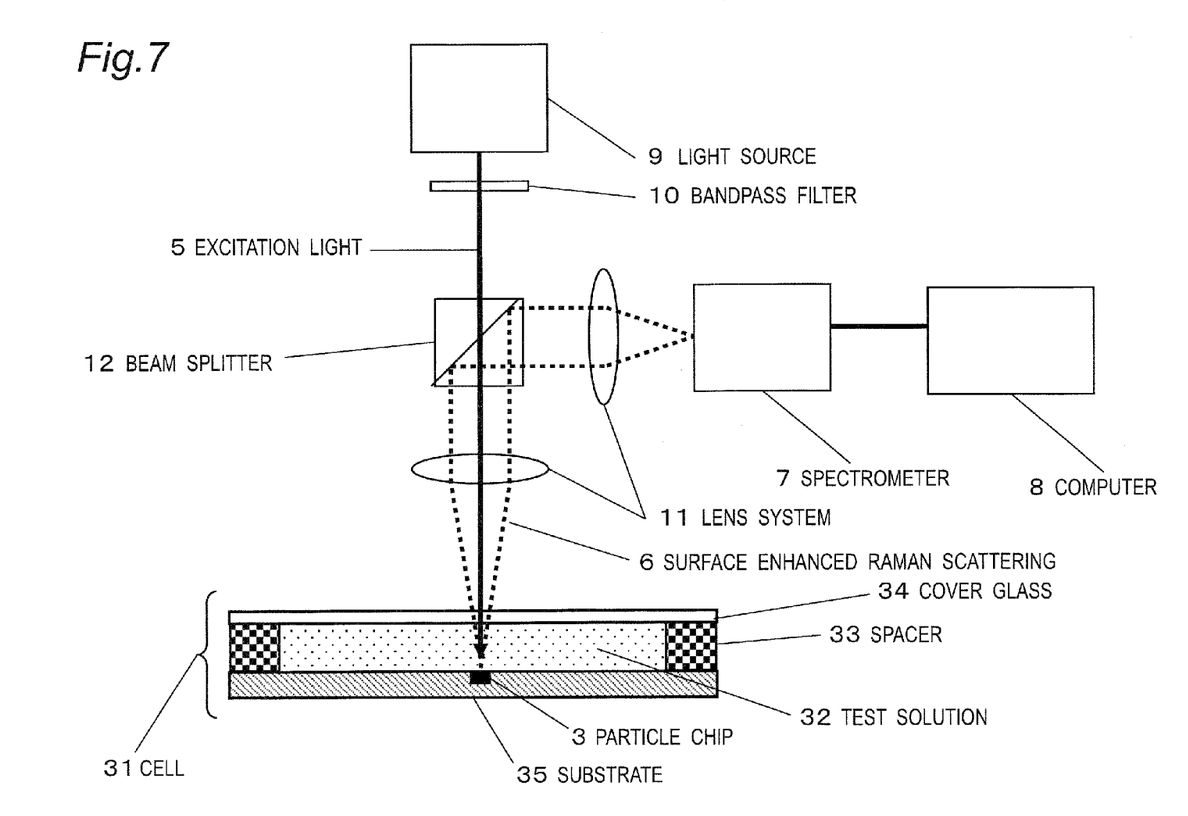
FIG. 7 is a schematic diagram showing the configuration of a measurement apparatus according to a third embodiment of the present invention.

Hereinafter, a method for measuring a concentration of a biogenic substance according to a third embodiment will be explained with referring to FIG. 7. In FIG. 7, the same components as those in FIG. 1 are denoted by the same numerals, and descriptions thereof are omitted. FIG. 7 is a schematic diagram showing the configuration of a measurement apparatus according to the third embodiment.

The third embodiment differs from the first embodiment in that the particle chip 3 is provided in a cell 31 and the concentration of a biogenic substance in a test solution 32 is measured.

The cell 31 includes a spacer 33, a cover glass 34, a substrate 35, an inlet (not shown) for injecting the test solution 32 to the cell 31, and an outlet (not shown) for discharging the test solution 32 from the cell 31. The substrate 35 is provided with a groove into which a microchip 3 is to be fitted. The microchip 3 is provided in the groove, and the test solution 32 is filled in a space formed by the spacer 33, the cover glass 34, and the substrate 35.

The cover glass 34 is not particularly limited as long as it is transparent with respect to excitation light 5 and surface enhanced Raman scattering 6. Moreover, it is preferred to subject the cover glass 34 to antireflection processing in order to minimize the reflection of the excitation light 5 and the reflection of the surface enhanced Raman scattering 6 at the interface of the cover glass 34.

The spacer 33 and the substrate 35 are not particularly limited as long as they are materials that can ensure mechanical strength for holding the test solution 32 and chemical stability for the test solution 32 and ensure stability when a known sterilization method is used.

The other configurations are the same as those in the first embodiment or the second embodiment, so that descriptions thereof are omitted.

The test solution 32 may be a body fluid extracted from the living body. For example, whole blood, blood plasma, blood serum, sweat, tear, urine, saliva, and the like can be measured as the test solution.

The biogenic substance is not limited to glucose, and it is possible to measure, as the concentration of the biogenic substance, the concentration of metabolic products such as albumin, cholesterol, triglyceride, creatinine, and creatine, and antibodies, hormones, and the like by subjecting the surface of metal particles 13 to processing suitable for the biogenic substance to be measured.

The operations of the method for measuring the concentration of a biogenic substance according to the third embodiment can be those in the first embodiment or the second embodiment, and therefore are omitted.

The present invention can be used in order to measure the concentration of a biogenic substance such as glucose in a living body.

What is claimed is:

1. A method for measuring a concentration of a biogenic substance, comprising steps of:

(a) preparing an apparatus for biogenic substance concentration measurement,
said apparatus comprising a light source, a polarization controller which controls a polarization of the light from said light source, a substrate which has periodic metal structures and generates surface enhanced Raman scattering light by being irradiated with light emitted from said light source, and spectroscopic means which disperses and detects said surface enhanced Raman scattering light, wherein
said periodic metal structure is arranged with a first distance in a first direction and with a second distance in a second direction,
said first distance is set to generate surface plasmon by matching a phase of the light emitted by said light source, and
said second distance is smaller than said first distance and the second distance is set between 300 nm and 350 nm;
(b) irradiating the substrate with the light emitted from the light source so as to generate the surface enhanced Raman scattering, wherein the polarization of said light is controlled along with said first direction by said polarization controller;
(c) detecting said generated surface enhanced Raman scattering with said spectroscopic means;
(d) recording an intensity of said surface enhanced Raman scattering detected in step (c);
(e) irradiating the substrate with the light emitted from the light source so as to generate the surface enhanced Raman scattering, wherein the polarization of said light is changed by said polarization controller;
(f) detecting said generated surface enhanced Raman scattering at said step (e) with said spectroscopic means;
(g) recording an intensity of said surface enhanced Raman scattering detected in step (f);
(h) determining a larger intensity of surface enhanced Raman scattering and recording said larger intensity by comparing the recorded intensity of the surface enhanced Raman scattering at said step (g) with the recorded intensity of the surface enhanced Raman scattering at step (d);
(i) calculating the maximum intensity of surface enhanced Raman scattering by repeating the steps of (e) to (h);
(j) calculating the concentration of the biogenic substance on the basis of said maximum intensity of surface enhanced Raman scattering calculated in said step (i).

2. A method according to claim 1, wherein
said first direction and said second direction are perpendicular to each other.

3. A method according to claim 1, wherein
said substrate is arranged in a sample solution containing the biogenic substrate; and
the concentration of the biogenic substance contained in the test solution is measured.

4. A method according to claim 1, wherein
said substrate is implanted into a skin of a living body; and
the concentration of the biogenic substance contained in the living body is measured.

5. A method according to claim 1, wherein
said biogenic substance is glucose.

* * * * *